(12) United States Patent  
Joe et al.

(10) Patent No.: US 9,023,824 B2  
(45) Date of Patent: May 5, 2015

(54) COMPOSITION FOR INHIBITING ANGIOGENESIS CONTAINING A PEROXIDASIN INHIBITOR AS AN ACTIVE INGREDIENT

(71) Applicant: Catholic University Industry Academic Cooperation Foundation, Seoul (KR)

(72) Inventors: Young Ae Joe, Seoul (KR); Hyun Kyung Kim, Yongin-si (KR)

(73) Assignee: Catholic University Industry Academic Cooperation Foundation, Seoul (KR)

( * ) Notice: Subject to any disclaimer, the term of this patent is extended or adjusted under 35 U.S.C. 154(b) by 0 days.

(21) Appl. No.: 14/185,842

(22) Filed: Feb. 20, 2014

(65) Prior Publication Data

US 2014/0171488 A1     Jun. 19, 2014

Related U.S. Application Data

(63) Continuation-in-part of application No. PCT/KR2011/008781, filed on Nov. 17, 2011.

(30) Foreign Application Priority Data

Aug. 22, 2011    (KR) .................... 10-2011-0083449

(51) Int. Cl.  
     *A61K 48/00*      (2006.01)  
     *C07H 21/02*      (2006.01)  
     *C07H 21/04*      (2006.01)  
     *A61K 31/713*      (2006.01)  
     (Continued)

(52) U.S. Cl.  
     CPC .......... *C12N 15/1137* (2013.01); *A61K 31/713* (2013.01); *C12N 2310/11* (2013.01); *C12N 2310/14* (2013.01); *C12N 2310/16* (2013.01); *C12Q 1/28* (2013.01); *C12Q 1/6876* (2013.01); *C12Y 111/01007* (2013.01);  
     (Continued)

(58) Field of Classification Search  
     USPC ........................................... 514/44; 536/24.5  
     See application file for complete search history.

(56) References Cited

U.S. PATENT DOCUMENTS 7,419,779 B2     9/2008    Lorens et al.

FOREIGN PATENT DOCUMENTS

KR     10-20110076845       7/2011

OTHER PUBLICATIONS

Shi et al., "Involvement of vascular peroxidase 1 in angiotensin II-induced vascular smooth muscle cell proliferation," Cardiovascular Research, 91, pp. 27-36, 2011.

*Primary Examiner* — Terra Cotta Gibbs  
(74) *Attorney, Agent, or Firm* — Joseph H. Kim; JHK Law

(57) ABSTRACT

The invention relates to a composition for angiogenesis inhibition comprising a peroxidasin inhibitor as an effective ingredient, and more particularly, to a method of screening angiogenesis inhibitor, which includes steps of treating a test agent, and analyzing peroxidasin gene expression or protein activity, and comparing peroxidasin gene expression or protein activity between a case treated with the test agent and a case not treated with the test agent. Accordingly, since the inhibitor of the peroxidasin expression or protein activity according to the present invention can effectively inhibit migration, proliferation and tube formation of endothelial cells, the inhibitor can be effectively used for preventing or treating a variety of diseases or conditions of the diseases derived from abnormal regulation of angiogenesis.

4 Claims, 5 Drawing Sheets  
(2 of 5 Drawing Sheet(s) Filed in Color)

(51) Int. Cl.
  *C12N 15/113* (2010.01)
  *C12Q 1/28* (2006.01)
  *C12Q 1/68* (2006.01)
  *G01N 33/573* (2006.01)

(52) U.S. Cl.
  CPC .......... *G01N 33/573* (2013.01); *G01N 2500/04* (2013.01); *G01N 2800/7014* (2013.01)

```
                              SEQUENCE LISTING

<160> NUMBER OF SEQ ID NOS: 12

<210> SEQ ID NO 1
<211> LENGTH: 4440
<212> TYPE: DNA
<213> ORGANISM: Artificial Sequence
<220> FEATURE:
<223> OTHER INFORMATION: peroxidasin cDNA sequence

<400> SEQUENCE: 1
atggccaagc gctccagggg ccccgggcgc cgctgcctgt tggcgctcgt gctgttctgc      60
gcctggggga cgctggccgt ggtggcccag aagccgggcg cagggtgtcc gagccgctgc     120
ctgtgcttcc gcaccaccgt gcgctgcatg catctgctgc tggaggccgt gcccgccgtg     180
gcgccgcaga cctccatcct agatcttcgc tttaacagaa tcagagagat ccaacctggg     240
gcattcaggc ggctgaggaa cttgaacaca ttgcttctca ataataatca gatcaagagg     300
atacctagtg gagcatttga agacttggaa aatttaaaat atctctatct gtacaagaat     360
gagatccagt caattgacag gcaagcattt aagggacttg cctctctaga gcaactatac     420
ctgcacttta atcagataga aactttggac ccagattcgt tccagcatct cccgaagctc     480
gagaggctat ttttgcataa caaccggatt acacatttag ttccagggac atttaatcac     540
ttggaatcta tgaagagatt gcgactggac tcaaacacac ttcactgcga ctgtgaaatc     600
ctgtggttgg cggatttgct gaaaacctac gcggagtcgg ggaacgcgca ggcagcggcc     660
atctgtgaat atcccagacg catccaggga cgctcagtgg caaccatcac cccggaagag     720
ctgaactgtg aaaggcccccg gatcacctcc gagccccagg acgcagatgt gacctcgggg     780
aacaccgtgt acttcacctg cagagccgaa ggcaacccca gcctgagat catctggctg     840 cgaaacaata tgagctgag catgaagaca gattcccgcc taaacttgct ggacgatggg     900
accctgatga tccagaacac acaggagaca gaccagggta tctaccagtg catggcaaag     960
aacgtggccg gagaggtgaa gacgcaagag gtgacccctca ggtacttcgg gtctccagct    1020
cgacccactt ttgtaatcca gccacagaat acagaggtgc tggttgggga gagcgtcacg    1080
ctggagtgca gcgccacagg ccaccccccg ccgcggatct cctggacgag aggtgaccgc    1140 acaccttgc cagttgaccc gcgggtgaac atcacgcctt ggcgggct ttacatacag       1200 aacgtcgtac aggggggacag cggagagtat gcgtgctctg cgaccaacaa cattgacagc    1260
gtccatgcca ccgctttcat catcgtccag gctcttcctc agttcactgt gacgcctcag    1320
gacagagtcg ttattgaggg ccagaccgtg gatttccagt gtgaagccaa gggcaacccg    1380
ccgcccgtca tcgcctggac caagggaggg agccagctct ccgtggaccg gcggcacctg    1440
gtcctgtcat cgggaacact tagaatctct ggtgttgccc tccacgacca gggccagtac    1500
gaatgccagg ctgtcaacat catcggctcc cagaaggtcg tggcccacct gactgtgcag    1560
cccagagtca ccccagtgtt tgccagcatt cccagcgaca caacagtgga ggtgggcgcc    1620
aatgtgcagc tcccgtgcag ctcccagggc gagcccgagc cagccatcac ctggaacaag    1680
gatggggttc aggtgacaga aagtggaaaa tttcacatca gccctgaagg attcttgacc    1740
atcaatgacg ttgccctgc agacgcaggt cgctatgagt gtgtggcccg gaacaccatt    1800
gggtcggcct cggtgagcat ggtgctcagt gtgaatgttc ctgacgtcag tcgaaatgga    1860
```

-continued

```
gatccgtttg tagctacctc catcgtggaa gcgattgcga ctgttgacag agctataaac      1920
tcaacccgaa cacatttgtt tgacagccgt cctcgttctc caaatgattt gctggccttg      1980
ttccggtatc cgagggatcc ttacacagtt gaacaggcac gggcgggaga aatctttgaa      2040
cggacattgc agctcattca ggagcatgta cagcatggct tgatggtcga cctcaacgga      2100
acaagttacc actacaacga cctggtgtct ccacagtacc tgaacctcat cgcaaacctg      2160
tcgggctgta ccgccaccg gcgcgtgaac aactgctcgg acatgtgctt ccaccagaag       2220
taccggacgc acgacggcac ctgtaacaac ctgcagcacc ccatgtgggg cgcctcgctg      2280
accgccttcg agcgcctgct gaaatccgtg tacgagaatg cttcaacac ccctcggggc       2340
atcaaccccc accgactgta caacgggcac gcccttccca tgccgcgcct ggtgtccacc      2400
accctgatcg ggacggagac cgtcacaccc gacgagcagt tcacccacat gctgatgcag      2460
tggggccagt tcctggacca cgacctcgac tccacggtgg tggccctgag ccaggcacgc      2520
ttctccgacg gacagcactg cagcaacgtg tgcagcaacg accccccctg cttctctgtc      2580
atgatccccc ccaatgactc ccgggccagg agcggggccc gctgcatgtt cttcgtgcgc      2640
tccagccctg tgtgcggcag cggcatgact cgctgctca tgaactccgt gtacccgcgg       2700
gagcagatca accagctcac ctcctacata gacgcatcca acgtgtacgg gagcacggag      2760
catgaggccc gcagcatccg cgacctggcc agccaccgcg gcctgctgcg gcagggcatc      2820
gtgcagcggt ccgggaagcc gctgctcccc ttcgccaccg gccgcccac ggagtgcatg       2880
cgggacgaga acgagagccc catcccctgc ttcctggccg ggaccaccg cgccaacgag       2940
cagctgggcc tgaccagcat gcacacgctg tggttccgcg agcacaaccg cattgccacg      3000
gagctgctca agctgaaccc gcactgggac ggcgacacca tctactatga gaccaggaag      3060
atcgtgggtg cggagatcca gcacatcacc taccagcact ggctcccgaa gatcctgggg      3120
gaggtgggca tgaggacgct gggagagtac cacggctacg accccggcat caatgctggc      3180
atcttcaacg cctccgccac cgcggccctt caggtttggcc acacgcttgt caacccactg      3240
cttaccggc tggacgagaa cttccagccc attgcacaag atcacctccc ccttcacaaa       3300
gctttcttct ctcccttccg gattgtgaat gagggcggca tcgatccgct tctcaggggg      3360
ctgttcgggg tggcggggaa aatgcgtgtg ccctcgcagc tgctgaacac ggagctcacg      3420
gagcggctgt ctccatggc acacacggtg gctctggacc tggcggccat caacatccag       3480
cggggccggg accacgggat cccaccctac cacgactaca gggtctactg caatctatcg      3540
gcggcacaca cgttcgagga cctgaaaaat gagattaaaa accctgagat ccgggagaaa      3600
ctgaaaaggt tgtatggctc gacactcaac atcgacctgt ttccggcgct cgtggtggag      3660
gacctggtgc ctggcagccg gctggccccc accctgatgt gtcttctcag cacacagttc      3720
aagcgcctgc gagatgggga caggttgtgg tatgagaacc ctggggtgtt ctccccggcc      3780
cagctgactc agatcaagca gacgtcgctg gccaggatcc tatgcgacaa gcggacaac       3840
atcacccggg tgcagagcga cgtgttcagg gtggcggagt ccctcacgg ctacggcagc       3900
tgtgacgaga tccccagggt agacctccgg gtgtggcagg actgctgtga agactgtagg      3960
accagggggc agttcaatgc ctttttcctat catttccgag gcagacggtc tcttgagttc      4020
agctaccagg aggacaagcc gaccaagaaa acaagaccac ggaaaatacc cagtgttggg      4080
agacaggggg aacatctcag caacagcacc tcagccttca gcacacgctc agatgcatct      4140
gggacaaatg acttcagaga gtttgttctg gaaatgcaga gaccatcac agacctcaga       4200
acacagataa agaaacttga atcacggctc agtaccacag agtgcgtgga tgccggggggc     4260
```

```
gaatctcacg ccaacaacac caagtggaaa aaagatgcat gcaccatttg tgaatgcaaa    4320
gacgggcagg tcacctgctt cgtggaagct tgccccccctg ccacctgtgc tgtccccgtg    4380
```
(note: verifying) 
```
gaatctcacg ccaacaacac caagtggaaa aaagatgcat gcaccatttg tgaatgcaaa    4320
gacgggcagg tcacctgctt cgtggaagct tgcccccctg ccacctgtgc tgtccccgtg     4380
aacatcccag gggcctgctg tccagtctgc ttacagaaga gggcggagga aaagccctag    4440
```

<210> SEQ ID NO 2
<211> LENGTH: 19
<212> TYPE: DNA
<213> ORGANISM: Artificial Sequence
<220> FEATURE:
<223> OTHER INFORMATION: Peroxidasin F primer

<400> SEQUENCE: 2
tcaacccact gctttaccg                                                  19

<210> SEQ ID NO 3
<211> LENGTH: 19
<212> TYPE: DNA
<213> ORGANISM: Artificial Sequence
<220> FEATURE:
<223> OTHER INFORMATION: Peroxidasin R primer

<400> SEQUENCE: 3
aggtcgatgt tgagtgtcg                                                  19

<210> SEQ ID NO 4
<211> LENGTH: 21
<212> TYPE: DNA
<213> ORGANISM: Artificial Sequence
<220> FEATURE:
<223> OTHER INFORMATION: siRNA-1F

<400> SEQUENCE: 4
gcaugacuuc gcugcucaut t                                               21

<210> SEQ ID NO 5
<211> LENGTH: 21
<212> TYPE: DNA
<213> ORGANISM: Artificial Sequence
<220> FEATURE:
<223> OTHER INFORMATION: siRNA-1R

<400> SEQUENCE: 5
augagcagcg aagucaugct t                                               21

<210> SEQ ID NO 6
<211> LENGTH: 21
<212> TYPE: DNA
<213> ORGANISM: Artificial Sequence
<220> FEATURE:
<223> OTHER INFORMATION: siRNA-2F

<400> SEQUENCE: 6
gcaucaaugc uggcaucuut t                                               21

<210> SEQ ID NO 7
<211> LENGTH: 21
<212> TYPE: DNA
<213> ORGANISM: Artificial Sequence
<220> FEATURE:
<223> OTHER INFORMATION: siRNA-2R

<400> SEQUENCE: 7
aagaugccag cauugaugct t                                               21

<210> SEQ ID NO 8
<211> LENGTH: 21
<212> TYPE: DNA
<213> ORGANISM: Artificial Sequence
<220> FEATURE:
<223> OTHER INFORMATION: siRNA-3F

<400> SEQUENCE: 8
gcgaaucuca cgccaacaat t                                              21

<210> SEQ ID NO 9
<211> LENGTH: 21
<212> TYPE: DNA
<213> ORGANISM: Artificial Sequence
<220> FEATURE:
<223> OTHER INFORMATION: siRNA-3R

<400> SEQUENCE: 9
uuguuggcgu gagauucgct t                                              21

<210> SEQ ID NO 10
<211> LENGTH: 18
<212> TYPE: DNA
<213> ORGANISM: Artificial Sequence
<220> FEATURE:
<223> OTHER INFORMATION: Scrambled siRNA-F

<400> SEQUENCE: 10
guucaggucc ggcgagtt                                                  18

<210> SEQ ID NO 11
<211> LENGTH: 21
<212> TYPE: DNA
<213> ORGANISM: Artificial Sequence
<220> FEATURE:
<223> OTHER INFORMATION: Scrambled siRNA-R

<400> SEQUENCE: 11
cucgccggac acgcugaact t                                              21

<210> SEQ ID NO 12
<211> LENGTH: 1479
<212> TYPE: PRT
<213> ORGANISM: Artificial Sequence
<220> FEATURE:
<223> OTHER INFORMATION: peroxidasin peptide sequence

<400> SEQUENCE: 12

```
Met Ala Lys Arg Ser Arg Gly Pro Gly Arg Arg Cys Leu Leu Ala Leu
1               5                   10                  15

Val Leu Phe Cys Ala Trp Gly Thr Leu Ala Val Val Ala Gln Lys Pro
            20                  25                  30

Gly Ala Gly Cys Pro Ser Arg Cys Leu Cys Phe Arg Thr Thr Val Arg
        35                  40                  45

Cys Met His Leu Leu Leu Glu Ala Val Pro Ala Val Ala Pro Gln Thr
    50                  55                  60

Ser Ile Leu Asp Leu Arg Phe Asn Arg Ile Arg Glu Ile Gln Pro Gly
65                  70                  75                  80

Ala Phe Arg Arg Leu Arg Asn Leu Asn Thr Leu Leu Leu Asn Asn Asn
                85                  90                  95

Gln Ile Lys Arg Ile Pro Ser Gly Ala Phe Glu Asp Leu Glu Asn Leu
            100                 105                 110
```

-continued

```
Lys Tyr Leu Tyr Leu Tyr Lys Asn Glu Ile Gln Ser Ile Asp Arg Gln
            115                 120                 125

Ala Phe Lys Gly Leu Ala Ser Leu Glu Gln Leu Tyr Leu His Phe Asn
        130                 135                 140

Gln Ile Glu Thr Leu Asp Pro Asp Ser Phe Gln His Leu Pro Lys Leu
145                 150                 155                 160

Glu Arg Leu Phe Leu His Asn Asn Arg Ile Thr His Leu Val Pro Gly
                    165                 170                 175

Thr Phe Asn His Leu Glu Ser Met Lys Arg Leu Arg Leu Asp Ser Asn
                180                 185                 190

Thr Leu His Cys Asp Cys Glu Ile Leu Trp Leu Ala Asp Leu Leu Lys
            195                 200                 205

Thr Tyr Ala Glu Ser Gly Asn Ala Gln Ala Ala Ile Cys Glu Tyr
        210                 215                 220

Pro Arg Arg Ile Gln Gly Arg Ser Val Ala Thr Ile Thr Pro Glu Glu
225                 230                 235                 240

Leu Asn Cys Glu Arg Pro Arg Ile Thr Ser Glu Pro Gln Asp Ala Asp
                    245                 250                 255

Val Thr Ser Gly Asn Thr Val Tyr Phe Thr Cys Arg Ala Glu Gly Asn
                260                 265                 270

Pro Lys Pro Glu Ile Ile Trp Leu Arg Asn Asn Asn Glu Leu Ser Met
            275                 280                 285

Lys Thr Asp Ser Arg Leu Asn Leu Leu Asp Asp Gly Thr Leu Met Ile
        290                 295                 300

Gln Asn Thr Gln Glu Thr Asp Gln Gly Ile Tyr Gln Cys Met Ala Lys
305                 310                 315                 320

Asn Val Ala Gly Glu Val Lys Thr Gln Glu Val Thr Leu Arg Tyr Phe
                    325                 330                 335

Gly Ser Pro Ala Arg Pro Thr Phe Val Ile Gln Pro Gln Asn Thr Glu
                340                 345                 350

Val Leu Val Gly Glu Ser Val Thr Leu Glu Cys Ser Ala Thr Gly His
            355                 360                 365

Pro Pro Pro Arg Ile Ser Trp Thr Arg Gly Asp Arg Thr Pro Leu Pro
        370                 375                 380

Val Asp Pro Arg Val Asn Ile Thr Pro Ser Gly Gly Leu Tyr Ile Gln
385                 390                 395                 400

Asn Val Val Gln Gly Asp Ser Gly Glu Tyr Ala Cys Ser Ala Thr Asn
                    405                 410                 415

Asn Ile Asp Ser Val His Ala Thr Ala Phe Ile Ile Val Gln Ala Leu
                420                 425                 430

Pro Gln Phe Thr Val Thr Pro Gln Asp Arg Val Val Ile Glu Gly Gln
            435                 440                 445

Thr Val Asp Phe Gln Cys Glu Ala Lys Gly Asn Pro Pro Pro Val Ile
        450                 455                 460

Ala Trp Thr Lys Gly Gly Ser Gln Leu Ser Val Asp Arg Arg His Leu
465                 470                 475                 480

Val Leu Ser Ser Gly Thr Leu Arg Ile Ser Gly Val Ala Leu His Asp
                    485                 490                 495

Gln Gly Gln Tyr Glu Cys Gln Ala Val Asn Ile Ile Gly Ser Gln Lys
                500                 505                 510

Val Val Ala His Leu Thr Val Gln Pro Arg Val Thr Pro Val Phe Ala
            515                 520                 525

Ser Ile Pro Ser Asp Thr Thr Val Glu Val Gly Ala Asn Val Gln Leu
```

```
                530              535            540
Pro Cys Ser Ser Gln Gly Glu Pro Glu Pro Ala Ile Thr Trp Asn Lys
545                 550             555                 560

Asp Gly Val Gln Val Thr Glu Ser Gly Lys Phe His Ile Ser Pro Glu
                565             570                 575

Gly Phe Leu Thr Ile Asn Asp Val Gly Pro Ala Asp Ala Gly Arg Tyr
                580              585                590

Glu Cys Val Ala Arg Asn Thr Ile Gly Ser Ala Ser Val Ser Met Val
            595                 600             605

Leu Ser Val Asn Val Pro Asp Val Ser Arg Asn Gly Asp Pro Phe Val
        610             615             620

Ala Thr Ser Ile Val Glu Ala Ile Ala Thr Val Asp Arg Ala Ile Asn
625             630             635             640

Ser Thr Arg Thr His Leu Phe Asp Ser Arg Pro Arg Ser Pro Asn Asp
                645             650             655

Leu Leu Ala Leu Phe Arg Tyr Pro Arg Asp Pro Tyr Thr Val Glu Gln
                660             665             670

Ala Arg Ala Gly Glu Ile Phe Glu Arg Thr Leu Gln Leu Ile Gln Glu
            675             680             685

His Val Gln His Gly Leu Met Val Asp Leu Asn Gly Thr Ser Tyr His
        690             695             700

Tyr Asn Asp Leu Val Ser Pro Gln Tyr Leu Asn Leu Ile Ala Asn Leu
705             710             715                 720

Ser Gly Cys Thr Ala His Arg Arg Val Asn Asn Cys Ser Asp Met Cys
                725             730             735

Phe His Gln Lys Tyr Arg Thr His Asp Gly Thr Cys Asn Asn Leu Gln
                740             745             750

His Pro Met Trp Gly Ala Ser Leu Thr Ala Phe Glu Arg Leu Leu Lys
            755             760             765

Ser Val Tyr Glu Asn Gly Phe Asn Thr Pro Arg Gly Ile Asn Pro His
770             775             780

Arg Leu Tyr Asn Gly His Ala Leu Pro Met Pro Arg Leu Val Ser Thr
785             790             795                 800

Thr Leu Ile Gly Thr Glu Thr Val Thr Pro Asp Glu Gln Phe Thr His
                805             810                 815

Met Leu Met Gln Trp Gly Gln Phe Leu Asp His Asp Leu Asp Ser Thr
            820             825             830

Val Val Ala Leu Ser Gln Ala Arg Phe Ser Asp Gly Gln His Cys Ser
        835             840             845

Asn Val Cys Ser Asn Asp Pro Pro Cys Phe Ser Val Met Ile Pro Pro
850             855             860

Asn Asp Ser Arg Ala Arg Ser Gly Ala Arg Cys Met Phe Phe Val Arg
865             870             875                 880

Ser Ser Pro Val Cys Gly Ser Gly Met Thr Ser Leu Leu Met Asn Ser
                885             890             895

Val Tyr Pro Arg Glu Gln Ile Asn Gln Leu Thr Ser Tyr Ile Asp Ala
            900             905             910

Ser Asn Val Tyr Gly Ser Thr Glu His Glu Ala Arg Ser Ile Arg Asp
        915             920             925

Leu Ala Ser His Arg Gly Leu Leu Arg Gln Gly Ile Val Gln Arg Ser
        930             935             940

Gly Lys Pro Leu Leu Pro Phe Ala Thr Gly Pro Pro Thr Glu Cys Met
945             950             955             960
```

```
Arg Asp Glu Asn Glu Ser Pro Ile Pro Cys Phe Leu Ala Gly Asp His
            965                 970                 975

Arg Ala Asn Glu Gln Leu Gly Leu Thr Ser Met His Thr Leu Trp Phe
            980                 985                 990

Arg Glu His Asn Arg Ile Ala Thr Glu Leu Leu Lys Leu Asn Pro His
            995                1000                1005

Trp Asp Gly Asp Thr Ile Tyr Tyr Glu Thr Arg Lys Ile Val Gly
           1010                1015                1020

Ala Glu Ile Gln His Ile Thr Tyr Gln His Trp Leu Pro Lys Ile
   1025                1030                1035

Leu Gly Glu Val Gly Met Arg Thr Leu Gly Glu Tyr His Gly Tyr
   1040                1045                1050

Asp Pro Gly Ile Asn Ala Gly Ile Phe Asn Ala Phe Ala Thr Ala
   1055                1060                1065

Ala Phe Arg Phe Gly His Thr Leu Val Asn Pro Leu Leu Tyr Arg
   1070                1075                1080

Leu Asp Glu Asn Phe Gln Pro Ile Ala Gln Asp His Leu Pro Leu
   1085                1090                1095

His Lys Ala Phe Phe Ser Pro Phe Arg Ile Val Asn Glu Gly Gly
   1100                1105                1110

Ile Asp Pro Leu Leu Arg Gly Leu Phe Gly Val Ala Gly Lys Met
   1115                1120                1125

Arg Val Pro Ser Gln Leu Leu Asn Thr Glu Leu Thr Glu Arg Leu
   1130                1135                1140

Phe Ser Met Ala His Thr Val Ala Leu Asp Leu Ala Ala Ile Asn
   1145                1150                1155

Ile Gln Arg Gly Arg Asp His Gly Ile Pro Pro Tyr His Asp Tyr
   1160                1165                1170

Arg Val Tyr Cys Asn Leu Ser Ala Ala His Thr Phe Glu Asp Leu
   1175                1180                1185

Lys Asn Glu Ile Lys Asn Pro Glu Ile Arg Glu Lys Leu Lys Arg
   1190                1195                1200

Leu Tyr Gly Ser Thr Leu Asn Ile Asp Leu Phe Pro Ala Leu Val
   1205                1210                1215

Val Glu Asp Leu Val Pro Gly Ser Arg Leu Gly Pro Thr Leu Met
   1220                1225                1230

Cys Leu Leu Ser Thr Gln Phe Lys Arg Leu Arg Asp Gly Asp Arg
   1235                1240                1245

Leu Trp Tyr Glu Asn Pro Gly Val Phe Ser Pro Ala Gln Leu Thr
   1250                1255                1260

Gln Ile Lys Gln Thr Ser Leu Ala Arg Ile Leu Cys Asp Asn Ala
   1265                1270                1275

Asp Asn Ile Thr Arg Val Gln Ser Asp Val Phe Arg Val Ala Glu
   1280                1285                1290

Phe Pro His Gly Tyr Gly Ser Cys Asp Glu Ile Pro Arg Val Asp
   1295                1300                1305

Leu Arg Val Trp Gln Asp Cys Cys Glu Asp Cys Arg Thr Arg Gly
   1310                1315                1320

Gln Phe Asn Ala Phe Ser Tyr His Phe Arg Gly Arg Arg Ser Leu
   1325                1330                1335

Glu Phe Ser Tyr Gln Glu Asp Lys Pro Thr Lys Lys Thr Arg Pro
   1340                1345                1350
```

-continued

```
Arg Lys Ile Pro Ser Val Gly Arg Gln Gly Glu His Leu Ser Asn
    1355            1360            1365

Ser Thr Ser Ala Phe Ser Thr Arg Ser Asp Ala Ser Gly Thr Asn
    1370            1375            1380

Asp Phe Arg Glu Phe Val Leu Glu Met Gln Lys Thr Ile Thr Asp
    1385            1390            1395

Leu Arg Thr Gln Ile Lys Lys Leu Glu Ser Arg Leu Ser Thr Thr
    1400            1405            1410

Glu Cys Val Asp Ala Gly Gly Glu Ser His Ala Asn Asn Thr Lys
    1415            1420            1425

Trp Lys Lys Asp Ala Cys Thr Ile Cys Glu Cys Lys Asp Gly Gln
    1430            1435            1440

Val Thr Cys Phe Val Glu Ala Cys Pro Pro Ala Thr Cys Ala Val
    1445            1450            1455

Pro Val Asn Ile Pro Gly Ala Cys Cys Pro Val Cys Leu Gln Lys
    1460            1465            1470

Arg Ala Glu Glu Lys Pro
    1475
```

COMPOSITION FOR INHIBITING ANGIOGENESIS CONTAINING A PEROXIDASIN INHIBITOR AS AN ACTIVE INGREDIENT

TECHNICAL FIELD

The invention relates to a composition for inhibiting angiogenesis comprising peroxidasin inhibitor as an effective ingredient, and more particularly to a pharmaceutical composition for inhibiting angiogenesis comprising peroxidasin inhibitor which effectively inhibits migration, proliferation and tube formation of endothelial cells, and a method for screening angiogenic inhibitor.

BACKGROUND ART

Angiogenesis is a process of generating new blood vessels from pre-existing ones, and is a vital process in normal innate defense mechanisms such as wound healing and inflammation, and biological phenomenon and early-stage development.

Further, angiogenesis is very important in terms of clinical application as well as basic medicine, considering its clinical therapeutic effect obtained by blocking angiogenesis in the diseases like cancer, diabetic retinopathy, psoriasis, or rheumathritis, and therapeutic effect obtained by inducing angiogenesis in the diseases derived from the lack of new vessels such as cardiac infarction or ischemic limb. Given this, studies in the molecular and cellular mechanisms of angiogenic process are considered to be a prototype that can have a variety of clinical applications.

Meanwhile, the angiogenic process involves a series of sequential steps including decomposition of basement membrane of vessels by proteolytic enzyme, tube formation of endothelial cells that constitute vessel walls by re-construction of blood vessels by migration, proliferation and differentiation of the endothelial cells and generation of new capillary vessels.

The angiogenic process is strictly regulated by a variety of negative and positive regulatory factors, because if not regulated normally, this can exacerbate various diseases including cancer, rheumathritis, or diabetic retinopathy. Abnormal angiogenesis is particularly known as playing a vital role in the growth and metastatis of tumor, considering, first, its operation of supplying nutrients and oxygen needed for the growth and proliferation of tumor, and second, the new capillary vessels which invade into the tumor and provide tumor cells a chance to get into the blood circulation system, thereby enabling the tumor cells to spread all over the body.

Accordingly, studies about the angiogenic mechanisms and development of new matters that can inhibit angiogenesis have gained increasing attention in the prevention and treatment of various diseases including cancer, and recently, the studies about angiogenic inhibitor have been accelerated as the pre-clinical experiments on animal tumor models and the clinical studies confirmed that the angiogenic inhibition can effectively inhibit the growth and development of tumor and prolong patients' lives. Further, such angiogenic inhibitor is particularly considered to be promising in the anticancer therapy, because, first, angiogenic inhibitor can be used universally in all types of solid tumors, second, while the conventional anticancer chemo-therapy has toxicity on the bone marrow cells and stomach system cells with relatively faster cell cycle due to its principle of targeting fast growth of cancer cells, the angiogenic inhibitor has relatively less side effects even for a long period of administration, third, it is possible to suppress many cancer cells through inhibition of one blood vessel cell, because one vessel cell can supply nutrients and oxygen to hundreds of cancer cells, and fourth, while the conventional anticancer therapy needs release of anticancer agent out of the vessel to influence the cancer cells, the angiogenic inhibitor directly contacts the endothelial cells to thus have facilitated drug delivery.

Theory about existence of the endothelial progenitor cells (EPC) circulating in the blood of an adult has been reported a hundred years ago, which was characterized in 1997 by Dr. Isner group and published for the first time in the Science. After that, many study groups have found evidences that indicate the existence of the endothelial progenitor cells (EPC) in the peripheral blood, bone marrow and umbilical cord blood. Particularly, it was confirmed that the EPC in the peripheral blood was derived from bone marrow, and it was reported that when the EPC cultured ex vivo was injected in vivo, the transplanted cells were incorporated into a site of angiogenesis in the ischemia animal models and xenograft tumor animal models, thereby contributing to angiogenesis. Studies have been actively undertaken about various growth factors and cytokine involved in the EPC migration.

The above shows changes in the paradigm of the angiogenesis in adults, and recently, it has been understood that the bone marrow EPC, as well as endothelial cells sprouting from the pre-existing blood vessels contribute to the angiogenesis.

However, while the therapeutic availability of EPC for ischemic tissue has been confirmed and clinical benefit has been expected. identification and characterization of EPCs have not been studied sufficiently. Markers that can distinguish from endothelial cells have not been developed, and far more has to be known about regulation of EPC differentiation.

Meanwhile, approximately 200 angiogenic inhibitors have been developed so far, which can be mainly characterized into four mechanisms of: lowering activity of a specific vascular growth factor; suppressing growth or inducing death of vascular endothelial cells; suppressing the action of indirect factors that regulate the vascular growth factor or the endothelial cell survival factors; and increasing the activity of the angiogenesis inhibitor present in body. The angiogenesis inhibitors such as angiostatin, endostatin, PK5, and prothrombin kringle 2 are particularly widely known.

Conventionally, study about how to inhibit signal transduction triggered by vascular endothelial growth factor (VEGF) for the purpose of inhibiting angiogenesis has been continued. In this case, angiogenesis appears to be suppressed in the early stage, but the vessels are formed more aggressively thereafter by acquisition of resistance. Considering the resistance and possible other disadvantageous side effects in vivo of the above-mentioned angiogenesis inhibitors, development of a new angiogenesis inhibitor with novel mechanism is necessary, which can resolve the problems occurring in the prior arts and also effectively suppress the angiogenesis.

DISCLOSURE

Technical Problem

In order to achieve the above-mentioned objects, a pharmaceutical angiogenic composition comprising an inhibitor of peroxidasin gene expression or an inhibitor of peroxidasin protein activity as an effective component, is provided.

Technical Solution

In one embodiment, the peroxidasin gene may consist of a sequence represented by SEQ. ID. NO: 1, and the peroxidasin protein may consist of an amino-acid sequence represented by SEQ. ID. NO: 12.

In one embodiment, the inhibitor of the gene expression or the inhibitor of the protein activity may be antisense nucleotide, siRNA, aptamer or antibody specific to peroxidasin.

In one embodiment, the siRNA may inhibit expression specifically to peroxidasin, and consists of a sequence selected from a group consisting of SEQ. ID. NO: 4 to 9.

In one embodiment, the inhibitor of the peroxidasin gene expression or the inhibitor of the peroxidasin protein activity may have an inhibitory activity against migration, proliferation or tube formation of endothelial cells.

In one embodiment, the composition may be for treatment or prevention of an angiogenesis-related disease selected from a group consisting of: diabetic retinopathy, retinopathy of prematurity, corneal graft rejection, neovascluar glaucoma, erythrosis, proliferative retinopathy, psoriasis, hemophilic joints, atheromatous capillary proliferation within atherosclerotic plaques, keloid, wound granulation, vascular adhesion, rheumatoid arthritis, osteoarthritis, autoimmune disease, Crohn's disease, recurrent stenosis, atheromatous arteriosclerosis, intestinal adhesion, cat scratch disease, ulcers, cirrhosis complications, glomerulonephritis, diabetic kidney disease, malignant nephrosclerosis, thrombotic microangiopathy, organ transplant rejection, glomerular neuropathy, diabetes, angiogenesis-dependent cancers, benign tumors, inflammatory diseases and nuerodegenerative diseases.

In one embodiment, a method of screening an angiogenesis inhibitor is provided, which may include steps of: treating a test agent, and analyzing peroxidasin gene expression or protein activity, and comparing peroxidasin gene expression or protein activity between a case treated with the test agent and a case not treated with the test agent.

In one embodiment, the method of screening may additionally include a step of determining the test agent to be an inhibitor of angiogenesis, if the case treated with the test agent has more inhibition of the peroxidasin gene expression or protein activity than the case not treated with the test agent.

In one embodiment, the analysis on the peroxidasin gene expression or protein activity may be carried out with one method selected from a group consisting of RT-PCR (Reverse Transcription Polymerase Chain Reaction), Northern blot, Western blot, cDNA microarray hybridization, in situ hybridization, radioimmunoassay, immuno-precipitation, immunohistochemistry, ELISA (enzyme-linked immunosorbent assay), and measurement of peroxidase activity.

In one embodiment, the angiogenesis inhibitor may be for treatment or prevention of an angiogenesis-related disease selected from a group consisting of: diabetic retinopathy, retinopathy of prematurity, corneal graft rejection, neovascluar glaucoma, erythrosis, proliferative retinopathy, psoriasis, hemophilic joints, atheromatous capillary proliferation within atherosclerotic plaques, keloid, wound granulation, vascular adhesion, rheumatoid arthritis, osteoarthritis, autoimmune disease, Crohn's disease, recurrent stenosis, atheromatous arteriosclerosis, intestinal adhesion, cat scratch disease, ulcers, cirrhosis complications, glomerulonephritis, diabetic kidney disease, malignant nephrosclerosis, thrombotic microangiopathy, organ transplant rejection, glomerular neuropathy, diabetes, angiogenesis-dependent cancers, benign tumors, inflammatory diseases and nuerodegenerative diseases.

Advantageous Effects

Since inhibiting expression of peroxidasin or protein activity according to the present invention can effectively inhibit migration of endothelial cells, cell proliferation and tube formation, it can be efficaciously used in the prevention or treatment of a variety of diseases derived from abnormal regulation of angiogenesis or conditions of such diseases, so that there is an effect that the peroxidasin can be used as a new target for the development of mechanism and treatment of angiogenesis-related diseases.

BRIEF DESCRIPTION OF DRAWINGS

The patent or application file contains at least one drawing executed in color. Copies of this patent or patent application publication with color drawing(s) will be provided by the Office upon request and payment of the necessary fee.

BEST MODE

Figure 1:
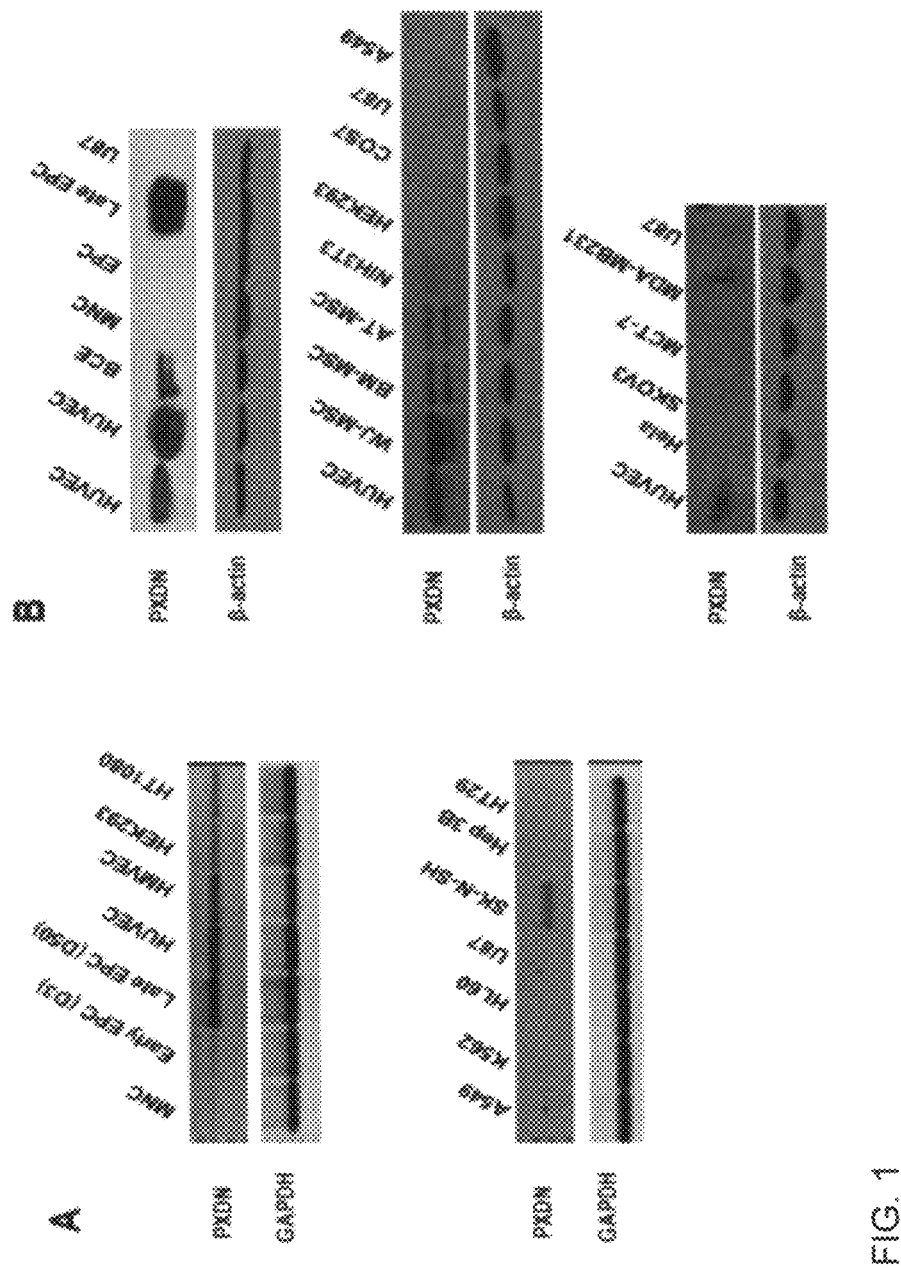
FIG. 1 presents analysis of expression pattern of peroxidasin on a variety of cells, in which A shows RT-PCR results and B shows result of western blot.

In order to achieve the above-mentioned objects, a pharmaceutical angiogenic composition comprising an inhibitor of peroxidasin gene expression or an inhibitor of peroxidasin protein activity as an effective ingredient, is provided.

An aspect of the present invention lies in the fact that the use of peroxidasin as a new target of treatment to prevent or treat angiogenesis-derived diseases is investigated and found for the first time, and that a pharmaceutical composition for angiogenesis inhibition comprising inhibitor of peroxidasin gene expression or inhibitor of proxidasin protein activity is provided.

The peroxidasin gene has been first reported in 1994 as peroxidasin homolog gene of *drosophilia* (Nelson et al., 1994), is one of myeloperoxidase family, and is unique protein having both peroxidase domain and extracellular domain. In the development of *Drosophila*, hemocytes differentiate from the head mesoderm in the early stage, make peroxidasin, and phagocytose. The principle mobile cells, hemocytes perform the joint function of the white blood cells of vertebrate and of insterstitial cell such as fibroblasts.

Further, hemocytes synthesize extracellular matrix such as collagen type IV (representative collagen distributed in blood vessels), laminin, glutactin, tiggrin, and proteoglycan papilin, and peroxidasin as they spread throughout the embryo.

Further, *Drosophila* peroxidasin consists of 1512 amino acid residues, and has trimeric structure. Human peroxidasin molecule consists of 1479 amino acids, and contains six (6) leucine-rich regions, and four (4) Ig loop and vWF type c sequences besides the peroxidase domain. In particular, the peroxidase domain as the enzyme domain is homologous with human myeloperoxidase (MPO) and eosinophil peroxidase. It has been observed that the peroxidase domain mediates the formation of $H_2O_2$-driven radio iodination, oxidation, dityrosine formation in vitro with peroxidase activity. Thus, peroxidasin is assumed to function in the extracelluar matrix consolidation, phagocytosis, and defence, but none has been confirmed clearly so far.

Meanwhile, based on the assumption that the peroxidasin gene has ECM domain and contributes to angiogenesis by being combined to the basement membrane, the present inventors have investigated the role of peroxidasin in angiogenesis.

First, according to one embodiment, in order to analyze the expression pattern of the peroxidasin, various cells were analyzed with RT-PCR and western blotting. As a result, it was confirmed that the peroxidasin was barely expressed in monocyte, expressed slightly in the early EPC, and strongly in the late EPC. It was also observed that the peroxidasin was expressed in the mature endothelial cells, which are HUVEC and HMVEC (See Example 1).

Further, according to another embodiment, as a result of analyzing expression pattern of the peroxidasin in the tissue through immunofluorescence and immunohistochemical staining, it was observed that the peroxidasin was expressed in the endothelial cells originated from both veins and arteries, and also from the small capillaries in the matrix portion (see Example 2).

Based on the above results, the present inventors could confirm that the peroxidasin is expressed strongly in the endothelial cells, and continued to construct siRNAs to inhibit the expression of the peroxidasin in order to investigate the role of the peroxidasin in the endothelial cells, and observed how they affect endothelial cells when the cells were treated with siRNAs.

First, in one embodiment, migration of endothelial cell according to inhibition of peroxidasin expression was analyzed. To do this, groups treated with siRNA for peroxidasin, and control groups including the group treated with the scrambled siRNA and untreated group were analyzed. As a result, it was observed that all the groups treated with siRNA for peroxidasin were affected to have a lower level of endothelial cell migration than those of the control groups (see Example 3).

Accordingly, it was assumed that peroxidasin was involved in the migration of endothelial cells and that it played an essential role in the migration of endothelial cells during angiogenesis.

Furthermore, in another embodiment, to investigate the possibility of inhibiting tube formation by inhibition of peroxidasin expression, HUVEC groups treated with siRNA for peroxidasin, and control groups including groups treated with scrambled siRNA and untreated groups were analyzed. As a result, the groups treated with siRNA for peroxidasin exhibited significantly reduced tube formation compared to the control groups (see Example 4).

Furthermore, it was also investigated that inhibiting the expression of peroxidasin also inhibited proliferation of the endothelial cells. That is, with bFGF stimulus, proliferation of endothelial cells was induced, and the groups treated with siRNA for peroxidasin and the groups treated with scrambled siRNA were compared with each other for degree of endothelial cell proliferation. As a result, the groups treated with siRNA for peroxidasin exhibited proliferation of endothelial cells reduced by 43% and 59.5% from those of the control groups (see Example 5).

Meanwhile, as mentioned above, angiogenesis is a highly-regulated process that occurs in response to various proangiogenic factors such as hypoxia and low pH, as well as growth factor, cytokine and other biological molecules. The angiogenesis mechanism for the development of new blood vessels requires cooperation of various molecules that regulate decomposition and reconstruction of the ECM, migration, proliferation, differentiation and tube formation, and upon initiation of the angiogenesis, angiogenic factors such as VEGF, bFGF, PDGF activate endothelial cells through stimulating the receptors at the surface of the cells and the activated cells go through proliferation, increasing expression of cell adhesion molecules, increasing secretion of proteolytic enzymes, increasing cell migration and invasion.

Further, new blood vessels are formed, as a plurality of molecules including proteolytic enzymes such as matrix metalloprotease and serine protease to decompose ECM, as well as the members of the integrin, selectin and immunoglobulin gene super family for cell adhesion, exert proliferation and invasion and also as the formation of lumens and differentiation into mature blood vessels are induced by the signal transduction mechanism originated from the receptors on the surface of the cells interacting with the ECM components and soluble factors.

Generally, in terms of new vessel formation, among all the cells, the vascular endothelial cell constructing the inner layer of the vessel and directly contacting the blood plays the central role as it regulates blood vessel dilation, thrombus inhibition, and transmission and migration of selective metabolites through the vessel wall by secreting various bioactive substances, and also regulates blood flow and attachment of leukocytes and thrombocytes by expressing various membrane proteins on the surface of the cell.

However, it was recently reported that not only the vascular endothelial cells, but also the endothelial progenitor cells (EPC) are involved in the construction of the blood vessels. That is, the EPC is known to promote angiogenesis by homing at neovascularization site while circulating in the blood in the form of progenitor cells that can differentiate into vascular endothelial cells.

Accordingly, based on the finding that the migration and proliferation of endothelial cells are effectively suppressed when the expression of peroxidasin is inhibited, the invention provides a pharmaceutical composition for angiogenesis inhibition comprising an inhibitor of peroxidasin gene expression or an inhibitor of peroxidasin protein as an effective component, which can prevent or treat angiogenesis-related diseases.

In one embodiment, the peroxidasin gene may include sequence represented by SEQ. ID. NO: 1, and may preferably consist of sequence represented by SEQ. ID. NO: 1. The peroxidasin protein may consist of amino acid coded from sequence represented by SEQ. ID. NO: 1, and preferably consist of amino acid sequence represented by SEQ. ID. NO: 12.

Further, the inhibitor of peroxidasin gene expression or the inhibitor of peroxidasin protein activity may be antisense oligonucleotide, siRNA, aptamer, antibody, compound or natural extract specific to peroxidasin.

The term "antisense oligonucleotide" used herein is intended to refer to nucleic acids, preferably, DNA, RNA or its derivatives, that are complementary to the base sequences of a target mRNA, characterized in that they bind to the target mRNA and interfere its translation to protein. The antisense oligonucleotide of the present invention refers to DNA or RNA sequences which are complementary to peroxidasin mRNA, characterized in that they bind to the peroxidasin mRNA and interfere its translation to protein, translocation into cytoplasm, or essential activities to other biological functions. The length of antisense oligonucleotide is in a range of 6-100 nucleotides, preferably 8-60 nucleotides, and more preferably 10-40 nucleotides.

The antisense oligonucleotide may be modified at above one or more positions of base, sugar or backbone to enhance its efficacy (De Mesmaeker et al., Curr Opin Struct Biol., 5(3):343-55(1995)). The oligonucleotide backbone may be modified by phosphothioate, phosphotriester, methyl phosphonate, single chain alkyl, cycloalkyl, single chain heteroatomic, heterocyclic bond between sugars, and so on. In addition, the antisense oligonucleotide may include one or more substituted sugar moieties. The antisense oligonucleotide may include a modified base. The modified base includes hypoxanthine, 6-methyladenine, 5-methylpyrimidine (particularly, 5-methylcytosine), 5-hydroxymethylcytosine (HMC), glycosyl HMC, gentobiosyl HMC, 2-aminoadenine, 2-thiouracil, 2-thiothymine, 5-bromouracil, 5-hydroxymethyluracil, 8-azaguanine, 7-deazaguanine, N6(6-aminohexyl)adenine, 2,6-diaminopurine, and so on. In addition, the antisense oligonucleotide may chemically bind to one or more moieties or conjugates which enhance activity of the antisense oligonucleotide or cell adhesion. There may be fat-soluble moiety including cholesterol moiety, cholesteryl, folic acid, thioeter, thiocholesterol, fatty chain, phosphatide, polyamine, polyethylene glycol chain, adamantane acetic acid, palmityl moiety, oxtadecylamine, hexylamino-carbonyl-oxycholesterol moiety, but not limited thereto. The method for preparing oligonucleotide containing fat-soluble moiety is well known in the technical field of the present invention (U.S. Pat. Nos. 5,138,045, 5,218,105, 5,459,255). The modified oligonucleotide enhances stability to nuclease and also enhances binding affinity between antisense oligonucleotide and the target mRNA.

The antisense oligonucleotide may be synthesized in vitro by the known method and administered in vivo, or alternatively, synthesized in vivo. One example of synthesizing antisense oligonucleotide in vitro is to use RNA polymerase I. One example of synthesizing antisense RNA in vivo is to use the vector with the origin of multicloning site (MCS) at an opposite direction to cause the antisense RNA transcription. It is preferable that the antisense RNA has the translation stop codon within the sequence to prevent translation into peptide sequence.

As used herein, the term "siRNA" refers to nucleic acid molecule that can mediate RNA interference or gene silencing (see: WO 00/44895, WO 01/36646, WO 99/32619, WO 01/29058, WO 99/07409 and WO 00/44914). Since siRNA can inhibit the expression of a target gene, it is used as an efficient gene knockdown method or gene therapeutic method. Although siRNA was first found in plants, bugs, *Drosophila* and parasite, siRNA was recently developed/used for the purpose of mammal cell research.

As used herein, the siRNA molecule may have a double-chain structure in which a sense strand (sequence corresponding to peroxidasin mRNA sequence) and an antisense strand (sequence complementary to peroxidasin mRNA sequence), or alternatively, the siRNA molecule may have a single-chain structure having self-complementary sense and antisense strand.

The siRNA of this invention is not restricted to a RNA duplex of which two strands are completely paired and may comprise non-paired portion such as mismatched portion with non-complementary bases and bulge with no opposite bases. The siRNA may be selected from a group consisting of sequences represented by SEQ. ID. NO: 4 to 9.

As used herein, the term "aptamer" refers to a nucleic acid molecule with binding activity to a specific target molecule. By binding to a specific target molecule, the aptamer can inhibit activity of the target molecule. In one embodiment, the aptamer may be RNA, DNA, modified nucleic acid or a combination thereof. In one embodiment, the aptamer may be in linear chain or angular shape. In one embodiment, the aptamer may have a length generally between about 15 and about 200 nucleotides, but not limited thereto. For example, the length of the aptamer may be below about 100 nucleotides, preferably below about 80 nucleotides, more preferably below about 60 nucleotides and most preferably below about 45 nucleotides. Further, in one embodiment, the length of the aptamer may be at least about 18, 20 or 25 nucleotides. If the total number of nucleotides is small, chemical synthesis and mass production are improved, cost effectiveness increases, and easy chemical modification, higher stability and lower toxicity for application on a living body are provided.

Further, as used herein, the aptamer may be prepared by the known method introduced by Ellington (Nature, 1990 346, 818-822; Tuerk et al., Science, 1990 249, 505-510). The 'SELEX' is used to screen oligonucleotides that specifically bind to a target substance in the pool of oligonucleotides having 10 to 14 different nucleotide sequences. The oligonucleotides as used herein has a structure in which random sequence of about 40 residues are inserted to the primer sequence. The oligonucleotide pool is associated with the target substance and the oligonucleotides which bind to the target substance are exclusively recovered using filter or the like. The recovered oligonucleotides are amplified with RT-PCR, and used as the prototype for the next round. The process is repeated about 10 times to acquire the aptamer specifically binding to the target substance. According to SELEX, the number of rounds may be increased, or binding substance is used to enable concentrating and screening of the aptamer with stronger binding force to the target substance. Accordingly, by regulating the number of rounds in SELEX, and/or varying the binding state, it is possible to obtain aptamer with different binding force, or aptamer with the same binding force but different sequences. Further, while SELEX includes amplification by the PCR, it is possible to carry out various modes of SELEX by applying variations such as by using manganese ion in the process.

Other than the conventional SELEX, Cell-SELEX may be used on a complex target, i.e., on living cells and tissues. The cell-SELEX provides an advantage since it enables development of aptamer for disease cells even before the surface marker target is not identified. Further, considering that the inherent characteristic is not exhibited in an isolated form, the cell-SELEX provides more advantages than the conventional SELEX, since the target protein in biological state enables more functional approach in the screening process.

In the present invention, antibody, peptide, compound or natural extract may be used as an inhibitor of peroxidasin protein activity, but not limited thereto.

In the present invention, the polyclonal or monoclonal antibody, and preferably monoclonal antibody may be used as an antibody to specifically bind to the peroxidasin protein. The antibody for the peroxidasin protein may be prepared by the conventional methods, e.g., fusion, recombinant DNA or phage antibody library. The general process for preparing antibody is well described in Harlow, E. and Lane, D., Using Antibodies: A Laboratory Manual, Cold Spring Harbor Press, New York, 1999; Zola, H., Monoclonal Antibodies: Manual of Techniques, CRC Press, Inc., Boca Raton, Fla., 1984; and Coligan, Current Protocols In immunology, Wiley/Greene, NY, 1991, the entirety of which is incorporated herein as a reference. For example, the hybridoma cell that produces monoclonal antibody is produced by fusing immortallized cell line with antibody-producing lymphocyte, the technique for which can be easily performed according to a method well known in the art. The polyclonal antibody can be obtained by injecting peroxidasin protein to a suitable animal, collecting antiserum from the animal, and isolating antibody from the antiserum using a known affinity technology. As used herein, the antibody may include single chain variable fragment (scFv). The single chain variable fragment may consist of "variable region (VL) of light chain-linker-variable region (VH) of heavy chain". The linker refers to a predetermined length of amino acid sequence which functions to artificially connect the variable regions of the light and heavy chains.

The peptide that specifically binds to peroxidasin to interfere with the activity of the peroxidasin may be obtained by the known general methods, e.g., by phage display method.

The compound to inhibit the activity of peroxidasin may be obtained by the following method, i.e., by the angiogenesis inhibitor screening method as provided by the present invention.

That is, the method for screening angiogenesis inhibitor may be provided according to the present invention, which may include the steps of: analyzing expression of peroxidasin gene or protein activity; and comparing the expression of peroxidasin gene and protein activity between when treated with the test substance and un-treated.

The method for analyzing expression of peroxidasin gene or protein activity may be performed by a variety of known methods in the art for the screening method of the present invention, which may include, but not limited to, one selected from the group consisting of RT-PCR (Reverse Transcription Polymerase Chain Reaction), nothern blotting, western blotting, cDNA microarray hybridization, in situ hybridization, radioimmunoassay, immuno-precipitation, immunohistochemistry and ELISA (enzyme-linked immunosorbent assay).

Further, in the method for screening according to the present invention, the test substance or peroxidasin protein may be marked as a detectable label. By way of example, the detectable label may be chemical label (e.g., biotin), enzyme label (e.g., horseradish peroxidase, alkaline phosphatase, peroxidase, luciferase, β-galactosidase and β-glucosidase), radioactive label (e.g., C14, I125, P32 및 S35), fluorescence label (e.g., coumarine, fluorescein, FITC (fluorescein Isothiocyanate), rhodamine 6G, rhodamine B, TAMRA (6-carboxy-tetramethyl-rhodamine), Cy-3, Cy-5, Texas Red, Alexa Fluor, DAPI (4,6-diamidino-2-phenylindole), HEX, TET, Dabsyl and FAM), luminescent label, chemiluminescent label, FRET (fluorescence resonance energy transfer) label or metal label (e.g., gold and silver).

By using the peroxidasin protein or test substance labeled with the detectable label, it is possible to analyze whether or not the peroxidasin protein and the test substance bind to each other by detecting a signal emitted from the label. By way of example, when alkaline phosphatase is used as the label, a signal is detected using substrate with color reaction such as bromochloroindolyl phosphate (BCIP), nitroblue tetrazolium (NBT), naphthol-AS-B1-phosphate and ECF (enhanced chemifluorescence). When the horse radish peroxidase is used as the label, a signal may be detected using the substrate such as chloronaphthol, aminoethyl cabazol, diaminobenzidine, D-luciferine, lucigenin (bis-N-methylacrydinium nitrate), resorufin benzyl ether, luminol, amplex red reagent (10-acetyl-3,7-dihydroxyphenoxazine), HYR (p-phenylene-diamine-HCl and pyrocatechol), TMB (tetramethylbenzidine), ABTS (2,2'-Azine-di[3-ethylbenzthiazoline sulfonate]), o-phenylendiamine (OPD) and naphthol/pyronin.

In the method for screening angiogenic inhibitor according to the present invention, the "test substance" refers to an unknown substance used in screening to investigate whether or not it influences the peroxidasin protein activity. The sample may contain chemical substance, peptide and natural extract, but not limited thereto. The sample analyzed by the screening method of the present invention is a single compound or a mixture of the compounds (e.g., natural extract or cell or tissue culture). The sample may be obtained from the synthetic or natural compound library. The method for obtaining the compound library is known in the art. The synthetic compound library is commercially available from Maybridge Chemical Co. (UK), Comgenex (USA), Brandon Associates (USA), Microsource (USA) and Sigma-Aldrich (USA), and the library of natural compounds is commercially available from Pan Laboratories (USA) and MycoSearch (USA). The sample can be obtained by a variety of known combinatory library methods such as, for example, biological library, spatially addressable parallel solid phase or solution phase libraries, synthetic library requiring deconvolution, "1-bead 1-compound" library, and synthetic library using hydrophilic chromatography screening. The method for synthesizing molecular library is disclosed in DeWitt et al., Proc. Natl. Acad. Sci. U.S.A. 90, 6909, 1993; Erb et al. Proc. Natl. Acad. Sci. U.S.A. 91, 11422, 1994; Zuckermann et al., J. Med. Chem. 37, 2678, 1994; Cho et al., Science 261, 1303, 1993; Carell et al., Angew. Chem. Int. Ed. Engl. 33, 2059, 1994; Carell et al., Angew. Chem. Int. Ed. Engl. 33, 2061; Gallop et al., J. Med. Chem. 37, 1233, 1994.

According to the method of the present invention, the degree of activity or expression of gene is measured from the peroxidasin protein treated with the test substance, and compared with that of the control group which is not treated with the test substance. If the expression or activity of peroxidasin is down-regulated, the test substance is determined to be an angiogenesis inhibitor and thus can be used as a treatment for the diseases related with angiogenesis.

According to the present invention, a pharmaceutical composition for angiogenesis inhibition may contain a pharmaceutically-effective amount of an inhibitor of peroxidasin protein gene expression or inhibitor of peroxidasin protein activity singularly, or may additionally contain one or more pharmaceutically-effective carriers, excipients or diluents.

As used herein, the expression 'pharmaceutically-effective amount' is an amount of the bioactive ingredient which is sufficient to show the intended biological or pharmacological activity when administered into animal or human. However, the pharmaceutically-effective amount may appropriately vary depending on the age, weight, health condition, gender, route of administration, or treatment period of a subject of administration.

As used herein, the expression 'pharmaceutically-acceptable' refers to a biologically-acceptable substance which does not generally cause gastroenteric trouble, allergic reaction such as dizziness, or any similar reaction, when administered to human. Examples of the carriers, excipients and diluents may include lactose, dextrose, sucrose, sorbitol, mannitol, xylitol, erithritol, maltitol, starchy, acacia rubber, alginate, gelatin, calcium phosphate, calcium silicate, cellulose, methyl cellulose, polyvinylpyrrolidone, water, methyl hydroxybenzoate, prophyl hydroxybenzoate, talc, magnesium stearate and preservative. Further, filler, anticoagulant, lubricant, wetting agent, fragrance, and preservative may be additionally included.

Further, the composition according to the present invention may be prepared into a dosage form using known methods to provide rapid, continuous or delayed release of the active component since administration into a mammalian animal, in various forms for oral or parenteral administration.

The representative example of a parenteral dosage form includes an injection dosage form which may be in liquid or suspension state. The injection dosage form may be prepared using the known techniques using appropriate dispersion or wetting agent and suspension. For example, it is possible to prepare an injection dosage form by dissolving the respective ingredients in saline solution or buffer solution. The oral dosage form includes, for example, ingestible tablet, buccal tablet, troche, elixir, suspension, syrup and wafer, which may include in addition to the effective ingredient, diluent (e.g., lactose, dextrose, sucrose, mannitol, sorbitol, cellulose and/or glycin) and lubricant (e.g., silica, talc, stearic acid and magnesium or calcium salts thereof and/or polyethylene glycol). The dosage form may include a binding agent such as magnesium aluminum silicate, starch paste, gelatin, tragacanth, methylcellulose, natrium carboxymethylcellulose and/or poly vinylpyrrolidine, and depending on cases, may additionally include disintegrating agent such as starch, agar, alginate or sodium, absorbent, colorant, flavor and/or sweetening agent. The dosage form may be prepared by the conventional mixing, granulation or coating.

Further, the composition according to the present invention may additionally include adjuvant such as preservative, water-dispersible powder, emulsification promoter, salts to adjust osmotic pressure or buffer, and other substances useful for treatment, and may be prepared into dosage form according to conventional methods.

The composition according to the present invention may be administered by the routes including oral, percutaneous, subcutaneous, intravenous or intramuscular administration. An amount of the active ingredient administered may be appropriately selected by considering various factors including administration route, age, gender, weight and severity of a patient. Further, the composition according to the present invention may be administered in parallel with a known compound to further increase the intended effect.

The administration route of the pharmaceutical composition according to the present invention into human and animal may include oral administration, or parenteral administration such as intravenous, subcutaneous, intranasal, or intraperitoneal administration. The oral administration includes sublingual application. The parenteral administration may include injection method such as subcutaneous, intramuscular and intravenous injections and drop method.

According to the composition of the present invention, the total effective amount of an inhibitor of the peroxidasin gene expression or peroxidasin protein activity may be administered at a single dose, or by the fractionated treatment protocol in which the inhibitor is administered at multiple doses for a long period of time. The content of the effective ingredient may vary depending on diseases, but generally, the effective amount of 100 μg to 3,000 mg for one dose may be administered repeatedly several times a day for an adult. However, the concentration of treatment or administration may be determined based on not only the route of administration and frequency of treatment, but also various other factors including patient's age, weight, health condition, gender, severity of disease, diet and excretion rate. Given the above, those skilled in the art will be able to determine an appropriate effective amount of administration that suits a specific use such as angiogenesis inhibition, or treatment or prevention of angiogenesis-related diseases, and the composition according to the present invention is not specifically limited to the specific dosage form, route of administration and method of administration that exhibit the effect of the present invention.

According to the present invention, a medicine for angiogenesis inhibition for prevention or treatment of angiogenesis-related diseases, comprising a pharmaceutical composition for angiogenesis inhibition according to the present invention as an effective ingredient may be provided, and a method for angiogenesis inhibition, comprising a step of administering an inhibitor of peroxidasin gene expression or peroxidasin protein activity according to the present invention into a mammalian animal except human with abnormally-continuing angiogenesis, may also be provided.

According to the present invention, the angiogenesis-derived diseases or diseases with abnormal angiogenesis may be selected from the group consisting of, but not limited to, diabetic retinopathy, retinopathy of prematurity, corneal graft rejection, neovascluar glaucoma, erythrosis, proliferative retinopathy, psoriasis, hemophilic joints, atheromatous capillary proliferation within atherosclerotic plaques, keloid, wound granulation, vascular adhesion, rheumatoid arthritis, osteoarthritis, autoimmune disease, Crohn's disease, recurrent stenosis, atheromatous arteriosclerosis, intestinal adhesion, cat scratch disease, ulcers, cirrhosis complications, glomerulonephritis, diabetic kidney disease, malignant nephrosclerosis, thrombotic microangiopathy, organ transplant rejection, glomerular neuropathy, diabetes, angiogenesis-dependent cancers, benign tumors, inflammatory diseases and nuerodegenerative diseases.

Hereinbelow, the examples of the present invention will be explained in greater detail. The following examples are provided to elucidate the present invention, but should not be construed as limiting.

EXAMPLES

Cell Culture

Cells and culture conditions used in the Examples of the present invention will be explained below. The HUVEC (human umbilical endothelial cell) was separated from the human cord by the known method of Jaffe et al. (see Clin. Invest. 52, 2745, 1973), and cultured in M199 medium added with 20% fetal bovine serum, 30 μg/ml endothelial cell growth supplement (BD Bioscience, USA), 90 μg/ml heparin (Sigma) and 1% antibiotic, and under condition of 37 temperature and supply of 5% carbon dioxide. Late EPC was cultured using the cells obtained by the previously-reported experiments (Ha et al, FEBS Lett. 581, 2663, 2007), and MNC and early EPC were also cultured in the said medium using the cells obtained by the previously-reported experiments (see FASEB J. 25, 159, 2011). The WJ-MSC was separated from the cord matrix portion using the method known by Mitchell et al. (Stem Cells, 21, 50, 2003), and cultured in Dulbecco's modified Eagle medium (DMEM) added with 10% fetal bovine serum. The bovine capillary endothelial cell (BCE) was obtained from the group of Tae-Hee Lee, Ph. D. of the Korea Institute of Radiological & Medical Sciences (Kim et al., Biochem, Biophy. Res. Commun., 304, 740), and AT-MSC was obtained from the team of Prof. Jong-won LEE of the Department of Plastic Surgery at Seoul St. Mary's Hospital and cultured in the said medium. The BM-MSC was purchased from Cambrex Bioscience (Rockland, Me.) and cultured using mesenchymal stem cell growth medium bullet-kit. The other cell lines were obtained from the American Tissue Culture Collection (Rockville, Md., USA). HL60 and Hep3B were cultured in RPMI-1640 medium added with 10% fetal bovine serum, and the rest cell lines were cultured in DMEM medium added with 10% fetal bovine serum.

Example 1

Peroxidasin Expression Pattern Analysis

<1-1> RT-PCR Analysis
In order to analyze the peroxidasin protein expression pattern in the respective cells cultured in the manners explained above, the total RNA was separated from the cells and RT-PCR was conducted. To do this, first, 1 ml of Trizol (Invitrogen, USA) reagent was added to the respective cells, left at room temperature for 3 minutes to allow complete separation of the nucleoprotein complex. 0.2 ml of chloroform was added per 1 ml of Trizol reagent, and the mixture solution was transferred to the tube and strongly agitated for 15 seconds and left abandoned for 3 minutes. After that, the solution was centrifuged for at 12000 rpm for 15 minutes at 4° C., and only the supernatant liquid was transferred to a new tube, added with isopropyl alcohol in volume corresponding to ½ of the volume of the supernatant liquid, left abandoned at room temperature for 10 minutes, and then centrifuged at 12000 rpm for 10 minutes at 4° C. After that, the supernatant liquid was removed, and the RNA pellet remaining on the bottom of the tube was washed with 70% ethanol. The RNA pellet was dried and dissolved in 50 ul of RNase-free distilled water.

To carry out RT-PCR, cDNA was synthesized using the reverse transcriptase system of Promega Corporation, and the acquired cDNA was amplified using the Super Taq PLUS version (Super Bio Co. LTD). The peroxidasin (hereinbelow, 'PXDN') gene was amplified using the primer descried below. At this time, the PCR carried out initial thermal denaturation at 95° C. for 5 minutes, denaturation at 95° C. for 1 minute, annealing at 55° C. for 5 minutes, and extension at 72° C. for 1 minute for 30 cycles and final extension at 72° C. for minutes. The PCR product was run in 1.0% agarose-gel electrophoresis, and visualized with EtBr reagent for observation of the reaction product.

Primer Sequence

```
Peroxidasin forward primer (SEQ. ID. No: 2):
5-TCA ACC CAC TGC TTT ACC G-3

Peroxidasin reverse primer (SEQ. ID. No: 3):
5-AGG TCG ATG TTG AGT GTC G-3
```

As a result of examining peroxidasin mRNA expression by RT-PCR, referring to FIG. 1, monocytes showed little expression, the early EPC showed a little expression, and the late EPC showed relatively high level of expression. It was also observed that the peroxidasin was highly expressed in the mature endothelial cells, HUVEC and HMVEC. Meanwhile, it was observed that A549, K562, HL60, U87, Hep3B, and HT29 were almost not expressed.

<1-2> Western Blot Analysis

The Western blot was used to examine the expression of peroxidasin in the respective cells of <1-1>. For the Western blot, first, the cultured cells were lysed in buffer (50 mM Tris (pH 8.0), 150 mM NaCl, 1% Triton X-100, 1% sodium deoxycholate, 0.1% SDS, 1 mM Na3VO4, 50 mM NaF, 1 mM EDTA, 1 mM EGTA, 2 mM PMSF, 1 µg/ml pepstatin, and protein inhibitor mixture (Roche)), and the cell lysate was centrifuged at 14000 rpm, 30 minutes. The supernatant liquid was subjected to 8% agarose gel electrophoresis. After that, the separated proteins were transferred to nitrocellulose membrane with 100V electricity for 2 hours, and the membrane was blocked with 5% skim milk. After incubating with primary antibody to PXDN, another reaction was conducted using horseradish peroxidase-linked secondary antibody. After immunologic reaction, the bands were visualized using the chemiluminscent substrate (ECL kit) (Amershan Pharmacia Biotech, Piscataway, N.J.).

Referring to FIG. 1B, the result of Western blot showed similar result as that of RT-PCR, which confirmed strong expression in HUVEC and late EPC, and moderate expression in bovine endothelial cells, thereby indicating that PXDN is highly expressed in the endothelial cells. Further, the relatively high level of peroxidasin expression was observed in the mesenchymal stromal cell of the newborn's umbilical cord matrix portion, while the expression was relatively less in the adult human bone marrow-derived and adipose tissue-derived mesenchymal stromal cell. The mouse-derived NIH3T3 had very weak expression possibly due to antibody's species specificity. Accordingly, it was confirmed that the peroxidasin is highly expressed mainly in the endothelial cells.

Example 2

Peroxidasin Expression Pattern Analysis in Cord Tissue

In order to observe the peroxidasin expression at the level of tissue, the present inventors analyzed the peroxidasin expression in the cord tissue where arteries and veins were clear. To do this, the cord tissue was analyzed by immunofluorescence and immunohistochemistry.

First, for immunoflurosent analysis, the human umbilical cord was fixed with 4% paraformaldehyde, made into paraffin block, and sectioned into 4 um in size. Paraffin was removed by xylene, and the tissue sections were rehydrated with alcohol. After that, unmasking was performed using an antibody retrieval method (0.1 mM Tris-EDTA buffer (pH 8.0), heating in microwave oven for 3 cycles×1 min). After incubating with 5% normal goat serum for 1 hour, each section was reacted with the primary antibody against peroxidasin protein overnight. After washing three times with PBS solution, each slide was incubated with the Alexa 488 or Cy 3-conjugated secondary antibody for 1 hour. The primary antibody and the concentration (dilution ratio) thereof was peroxidasin (1:500), CD31 (clone JC70A, 1:25, DAKO, Glostrup, Denmark), and vWF (clone F8/86, 1:25, DAKO, Glostrup, Denmark), and the control group used PBS solution instead of the primary antibody. After the antibody reaction, as a last step, each section was counterstained with 1 µg/ml DAPI (Sigma, St. Louis, Mo.).

Further, in the immunohistochemistry, the sections of human umbilical cord tissue treated with xylene and rehydrated with alcohol for the immunofluorescent analysis were treated with 3% hydrogen peroxide to quench endogenous peroxidase, blocked with 5% normal goat serum buffer for 1 hour, and allowed to react with the primary antibody overnight. Then, the sections were washed with PBS solution three times for 10 minutes each time, and allowed to react with the secondary antibody. The peroxidasin antibody (1:500) was used for the primary antibody, and chromagen 3,3-diaminobenzidine (DAB) (Sigma, St. Louis, Mo.) was used for visualization.

Figure 2:
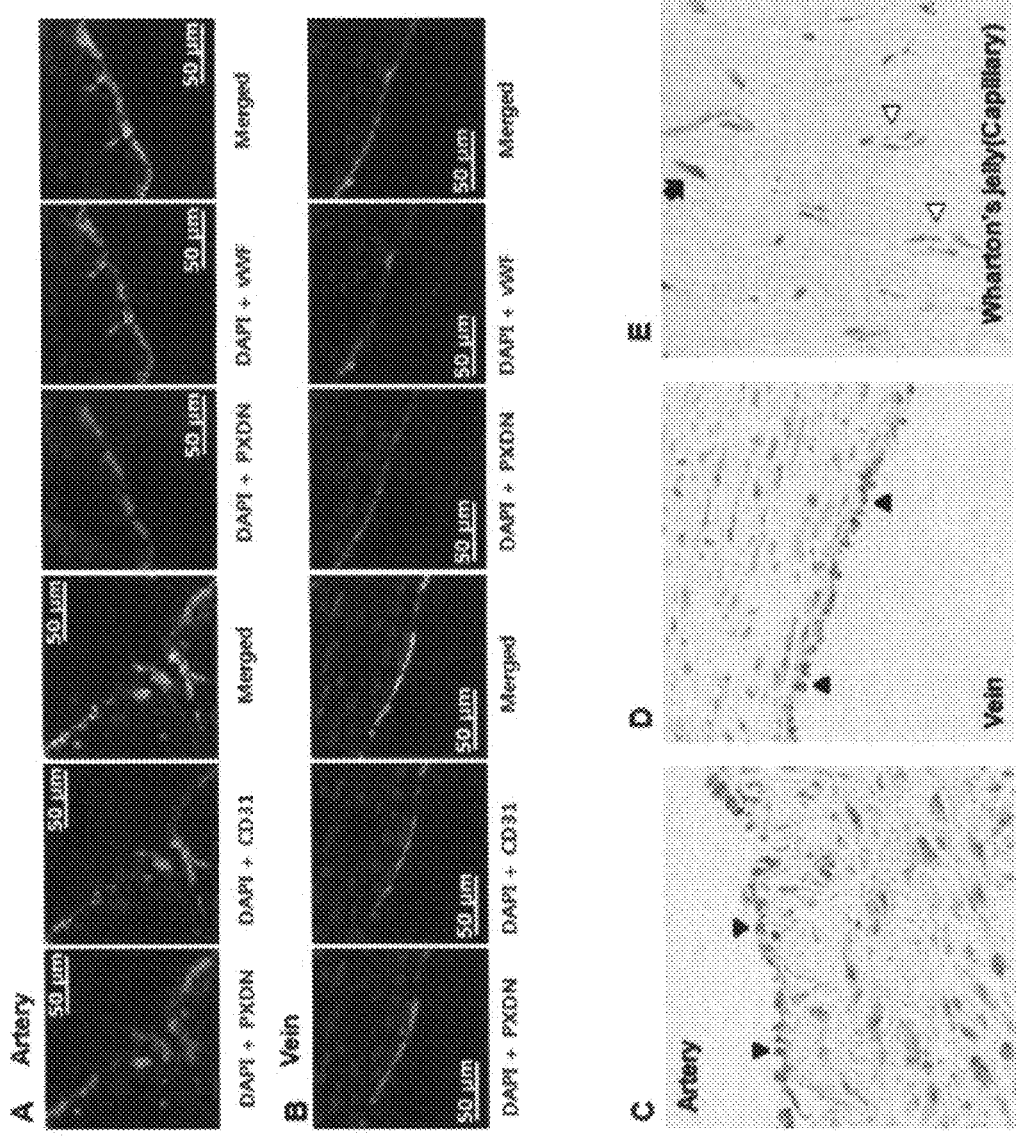
FIG. 2 shows photographs of immunofluorescence (A and B) and immunohistochemical staining (C-E) for peroxidasin expression pattern in human umbilical cord tissue.

The analysis results by immunofluorescence and immunohistochemistry confirmed peroxidasin expression in both the artery- and vein-derived endothelial cells since it was observed that the peroxidasin (red) expression site corresponds to CD31 (green) and vWF (green) expression sites. Further, the peroxidasin expression was also observed in the small capillaries of the matrix portion (see FIG. 2).

Accordingly, based on the above-mentioned results, the present invention could confirm that the peroxidasin is expressed in not only endothelial cells, but also stromal cells at the cord matrix (Wharton's jelly) portion.

Example 3

Analysis on Inhibition of Cell Migration by Peroxidasin Knockdown

Through the results of experiments explained above, the present inventors could confirm that the peroxidasin is expressed in the endothelial cells. Accordingly, based on such results, the present inventors investigated if peroxidasin is involved in the migration of the endothelial cells by analyzing if the peroxidasin, when inhibited in expression in the endothelial cells, affects the migration of the endothelial cells. To do this, the present inventors prepared siRNAs which can bind to different loci of the peroxidasin mRNA to inhibit peroxidasin expression, and also used the scrambled siRNA supplied by the ST Pham (Seoul, South Korea) as a control group. The prepared siRNA was treated with the HUVEC which was seeded at an amount of $5 \times 10^5$ cells/100 mm dish, in which the cells were cultured in M199 medium added with 20% fetal bovine serum, 30 µg/ml of endothelial cell growth supplements and 90 µg/ml heparin. The siRNA treatment of the HUVEC was conducted by treating with 10 nM (100 pmol) of scrambled siRNA and 10 nM (100 pmol) of peroxidasin siRNA with lipofectamine RNAiMAX Transfection Reagent (Invitrogen, Eugene, Oreg., USA) and culturing the treated cells for 48 hours.

The degree of migration of the endothelial cells treated with siRNA was analyzed by the method of Kim et al., (Mol Cancer Ther, 2133-2141, 2008). That is, the cells treated with siRNA and cultured for 48 hours were allowed to migrate in the presence of VEGF (2 ng/ml) for 5 hours. The migrated cells were then fixed and stained using hematoxylin and eosin, and photographed for analysis. Further, the degree of peroxidasin expression inhibition by siRNA treatment was analyzed in the same manner as the Western blot explained above.

TABLE 1 siRNA sequence

| Name | Forward direction | SEQ. ID. No: | Reverse direction | SEQ. ID. No: |
|---|---|---|---|---|
| siRNA-1 | GCA UGA CUU CGC UGC UCA UTT | 4 | AUG AGC AGC GAA GUC AUG CTT | 5 |
| siRNA-2 | GCA UCA AUG CUG GCA UCU UTT | 6 | AAG AUG CCA GCA UUG AUG CTT | 7 |
| siRNA-3 | GCG AAU CUC ACG CCA ACA ATT | 8 | UUG UUG GCG UGA GAU UCG CTT | 9 |
| Scrambled siRNA | GUU CAG GUC CGG CGA GTT | 10 | CUC GCC GGA CAC GCU GAA CTT | 11 |

Figure 3:
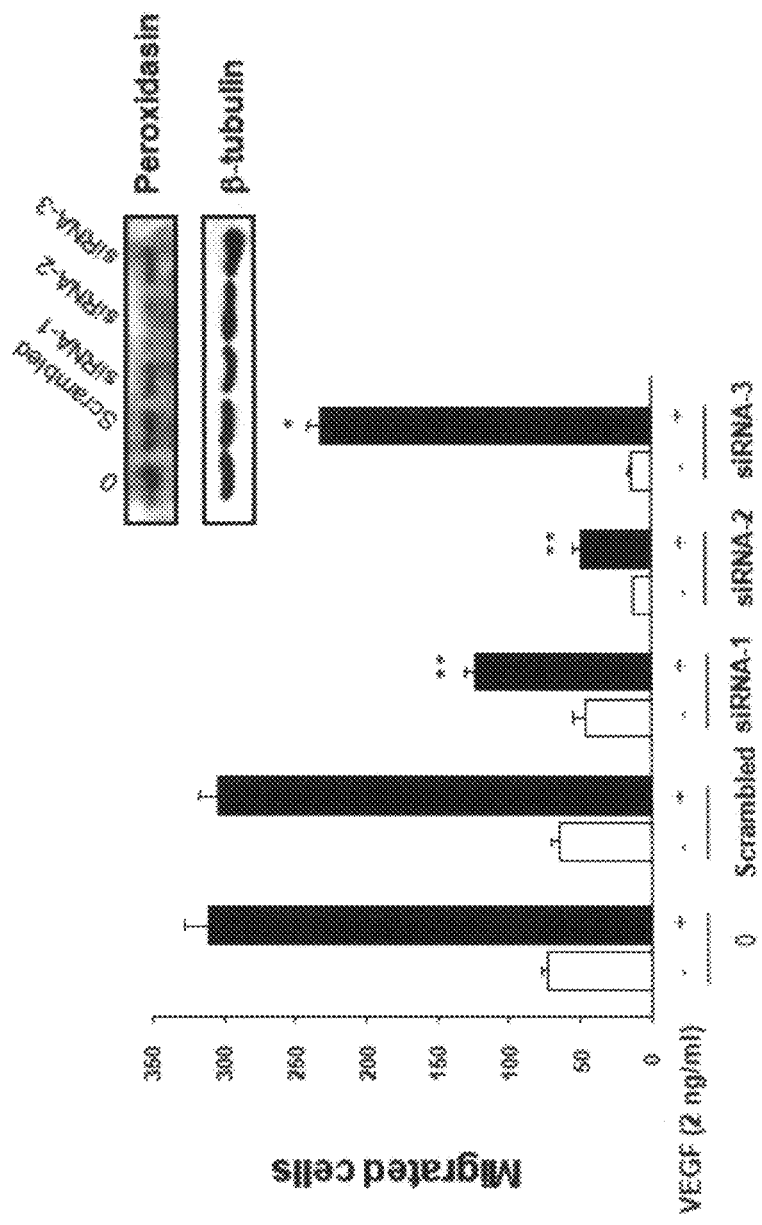
FIG. 3 is a graph presenting analysis result of pattern of inhibiting migration of endothelial cells according to treatment with siRNA for peroxidasin.

As a result, as FIG. 3 indicates, after preparing treating HUVECs with three types of siRNA binding to different loci on the peroxidasin mRNA, followed by 48-hour culture, decrease in the peroxidasin expression was observed in the HUVEC. Further, when the migration of the 48-hour-old cells after the transfection were induced in the modified Boyden chamber under the presence of VEGF ng/ml, it was observed that the cells transfected with the scrambled siRNA had similar degree of cell migration as the un-treated cells, while the cells transfected with siRNA1, siRNA2, and siRNA3 had lower degree of migration. Among these, the cells treated with siRNA2 in which peroxidasin expression is significantly reduced, showed significantly reduced cell migration.

Accordingly, based on the results of experiments discussed above, the present inventors could confirm that the peroxidasin plays a vital role in the migration of endothelial cells, and that it is possible to reduce the migration of endothelial cells by inhibiting peroxidasin expression or activity.

Example 4

Analysis on Inhibition of Tube Formation by Peroxidasin Knockdown

Since the present inventors could confirm through Example 3 that it is possible to inhibit the migration of endothelial cells by inhibiting peroxidasin expression, the inventors continued to investigate if it is also possible to inhibit tube formation by inhibiting the peroxidasin expression. To do this, the inventors added cold Matrigel (150 µl, BD Bioscience) to cell culture plate, allowed the same to harden at 37° C. 30 min. Then, the harvested cells transfected with siRNA1, siRNA2, or siRNA3 from Example 3, were plated on the Matrigel-coated cell culture plates and cultured for 20 hours more. After that, the tube formation was photographed for observation, and the size (i.e., length) of the tubes was measured using Image J (http://rsb.info.nih.gov/ij/) program.

Figure 4:
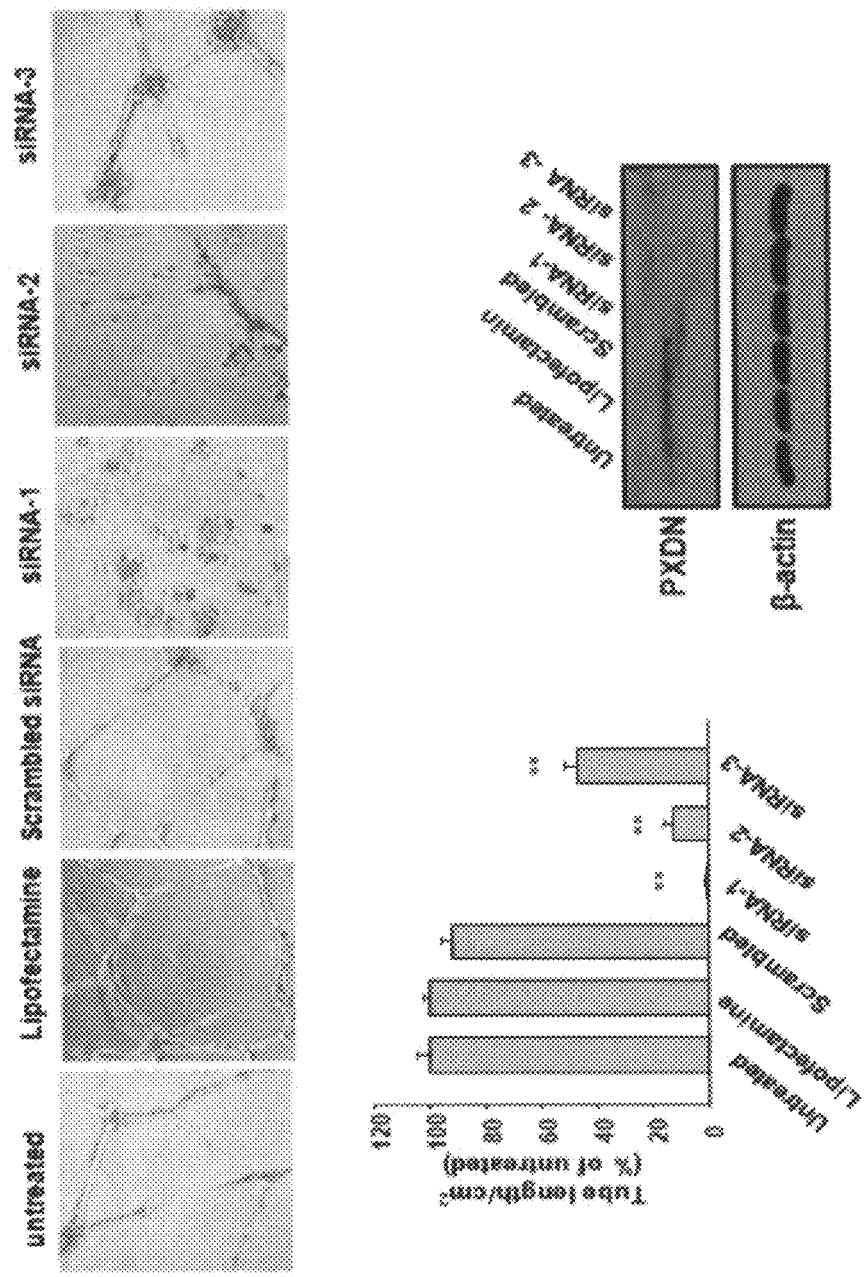
FIG. 4 is a graph presenting analysis result of degree of inhibiting tube formation of endothelial cells according to treatment with siRNA for peroxidasin.

As a result, as FIG. 4 indicates, a significantly-reduced tube formation of the endothelial cells was observed in the cells treated with siRNA for peroxidasin. Accordingly, the result confirmed that the peroxidasin plays an important role in the tube formation, and that it is possible to inhibit angiogenesis by regulating the same.

Example 5

Analysis on Inhibition of Endothelial Cell Proliferation by Peroxidasin Knockdown Using the siRNAs validated through the experiments discussed above, interrelation between peroxidasin and proliferation of endothelial cells was investigated by comparing the degrees of cell proliferation among the PXDN siRNA-treated group, scrambled siRNA-treated group, and lipofectamine-treated group. To do this, $4 \times 10^3$ cells (HUVECs) were seeded into 96-well plate, respectively, cultured for 24 hours, treated with siRNA1, siRNA3, scrambled siRNA or lipofectamine alone for 4 hours, respectively, and cultured for 48 hours. After culturing, the sample was treated with 20 ul MTS reagent, and the degree of cell proliferation was analyzed by measuring the absorbance of the respective cell plate at 490 nm with the ELISA reader (Molecular Devices, Sunnyvale, Calif., USA).

Figure 5:
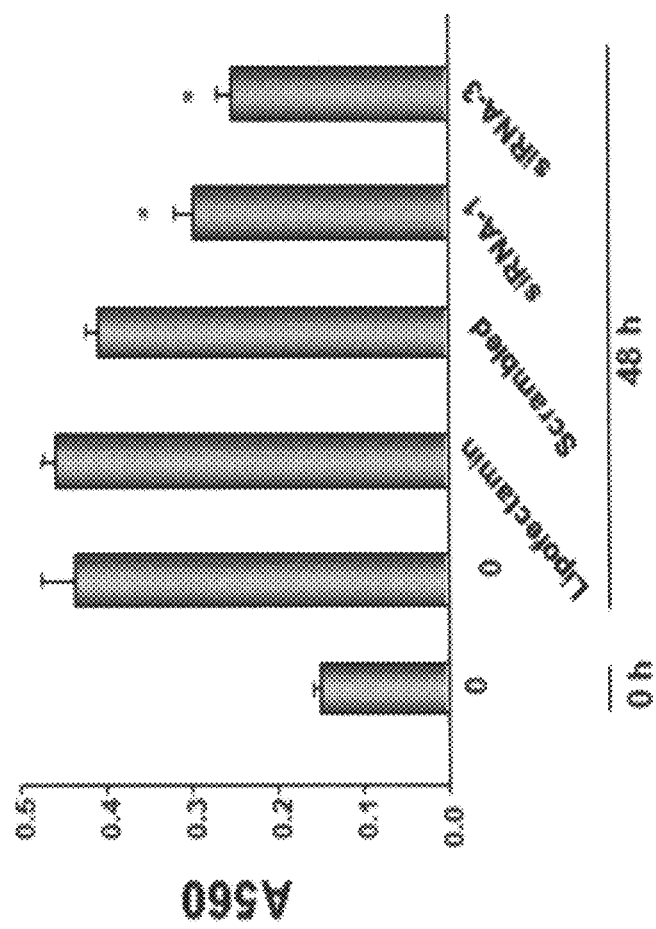
FIG. 5 is a graph presenting comparison analysis result of degree of inhibiting proliferation of endothelial cells according to treatment with siRNA for peroxidasin.

As a result, referring to FIG. 5, the cell groups treated with siRNA1 and siRNA3 respectively showed reduced proliferation by 43% and 59.5% from the cell group treated with the scrambled siRNA, respectively. Given the above, the present inventors could confirm that peroxidasin also plays an important role in the proliferation of the endothelial cells, and that in particular, it is effective to inhibit the proliferation of endothelial cells by inhibiting the peroxidasin expression or activity.

To sum up, the present inventors confirmed the fact that the peroxidasin plays an important role in the migration, proliferation and tube formation of the endothelial cells through the experiments as those explained above, that a substance which can inhibit peroxidasin expression or peroxidasin activity can be used as a treatment for the diseases related to angiogenesis, and that peroxidasin can be a new target for investigation on treatment and mechanism of angiogenesis-related diseases.

While several particular formulations have been described above, it will be apparent that various modifications and combinations of the formulations detailed in the text can be made without departing from the spirit and scope of the invention. Accordingly, the description of the exemplary embodiments of the present invention is intended to be illustrative, and not to limit the scope of the claims, and many alternatives, modifications, and variations will be apparent to those skilled in the art.

The invention claimed is:

1. A method for inhibiting angiogenesis in a subject, the method comprising administering to the subject an inhibitor of a peroxidasin gene expression or an inhibitor of a peroxidasin protein activity as an effective ingredient, wherein the inhibitor of the gene expression or the inhibitor of the protein activity is siRNA, wherein the siRNA inhibits expression of peroxidasin, and is selected from a sequence selected from the group consisting of SEQ ID NOS:4 to 9.

2. The method set forth in claim 1, wherein the peroxidasin gene has a nucleotide sequence as set forth in SEQ. ID. NO: 1, and the peroxidasin protein has an amino-acid sequence as set forth in SEQ. ID. NO: 12.

3. The method set forth in claim 1, wherein the inhibitor of the peroxidasin gene expression or the inhibitor of the peroxidasin protein activity has an inhibitory activity against migration, proliferation or tube formation of endothelial cells.

4. A method for treating an angiogenesis-related disease in a subject selected from the group consisting of: diabetic retinopathy, retinopathy of prematurity, corneal graft rejection, neovascular glaucoma, erythrosis, proliferative retinopathy, psoriasis, hemophilic joints, atheromatous capillary proliferation within atherosclerotic plaques, keloid, wound granulation, vascular adhesion, rheumatoid arthritis, osteoarthritis, autoimmune disease, Crohn's disease, recurrent stenosis, atheromatous arteriosclerosis, intestinal adhesion, cat scratch disease, ulcers, cirrhosis complications, glomerulonephritis, diabetic kidney disease, malignant nephrosclerosis, thrombotic microangiopathy, organ transplant rejection, glomerular neuropathy, diabetes, angiogenesis-dependent cancers, benign tumors, inflammatory diseases and nuerodegenerative diseases, comprising administering to the subject an inhibitor of a peroxidasin gene expression or an inhibitor of a peroxidasin protein activity as an effective ingredient, wherein the inhibitor of the gene expression or the inhibitor of the protein activity is siRNA, wherein the siRNA inhibits expression of peroxidasin, and is selected from a sequence selected from the group consisting of SEQ ID NOS:4 to 9.

* * * * *